United States Patent [19]

Kreuzer et al.

[11] Patent Number: 4,808,158
[45] Date of Patent: Feb. 28, 1989

[54] VASCULAR CATHETER

[75] Inventors: Rudolf Kreuzer, Munich, Fed. Rep. of Germany; Wayne A. Noda, Mission Viejo, Calif.; Friedemann Stockert, Munich, Fed. Rep. of Germany; Paul F. Zupkas, Costa Mesa, Calif.

[73] Assignee: Stockert Instrumente GmbH, Munich, Fed. Rep. of Germany

[21] Appl. No.: 143,255

[22] Filed: Jan. 4, 1988

Related U.S. Application Data

[63] Continuation of Ser. No. 880,762, Jul. 1, 1986, abandoned.

[30] Foreign Application Priority Data

Jul. 1, 1985 [DE] Fed. Rep. of Germany ....... 3523520

[51] Int. Cl.⁴ .............................................. A61M 31/00
[52] U.S. Cl. ................................ 604/49; 128/DIG. 3; 604/122; 604/170; 604/256
[58] Field of Search .......................... 604/4, 49, 51–54, 604/93, 96, 122, 164–170, 246, 249, 250, 256, 264, 266–268, 280, 282–284; 128/348.1, DIG. 3

[56] References Cited

U.S. PATENT DOCUMENTS

| | | | |
|---|---|---|---|
| 918,437 | 4/1909 | Genung | 604/170 |
| 2,012,363 | 8/1935 | Vogel | 604/267 |
| 2,628,404 | 2/1953 | Myers | 27/24 A |
| 3,406,685 | 10/1968 | May | 604/164 |
| 3,595,241 | 7/1971 | Sheridan | 27/24 A |
| 3,703,899 | 11/1972 | Calinog | 604/267 |
| 4,129,129 | 12/1978 | Amrine | 604/49 |
| 4,177,814 | 12/1979 | Krepshield et al. | 604/167 |
| 4,285,341 | 8/1981 | Pollack | 604/53 |
| 4,309,994 | 1/1982 | Grunwald | 604/284 |
| 4,385,633 | 5/1983 | Child | 604/246 |
| 4,639,252 | 1/1987 | Kelly et al. | 604/282 |
| 4,680,029 | 7/1987 | Ranford et al. | 604/4 |

OTHER PUBLICATIONS

Tanaka et al; "Transapical Aortic Perfusion witha double-Barreled Cannula"; 25 The annals of Thoracic Surgery, 209; (1981).

Reed, "Cannulation"; Cardiopulmonary Perfusion 228 (1975).

Taylor et al; #55 Symposium on Surgical Techniques 1205 (1975).

Primary Examiner—Stephen C. Pellegrino
Assistant Examiner—Mario Costantino
Attorney, Agent, or Firm—P. C. Richardson; L. C. Akers; R. C. Turner

[57] ABSTRACT

A vascular catheter for cannulating arterial or venous vessels, for example in the fermoral region, or the vena cava and/or the right auricle of the heart, comprises a flexible tube having blood passage orifices in the nature of holes at its anterior and insertion end to be inserted in the vessel or the auricle, which tube is directly or indirectly connectable at its other open end to a conduit or appliance. A piston-like closure member is movable to and fro in the tube in lengthwise direction thereof, such that it covers and thereby closes at least same of the blood passsage orifices in one position in the tube and clears these orifices in other positions. Preferably, the closure member is so fashioned that in its closure position, it covers all blood passage orifices in the insertion end of the cathether tube.

3 Claims, 2 Drawing Sheets

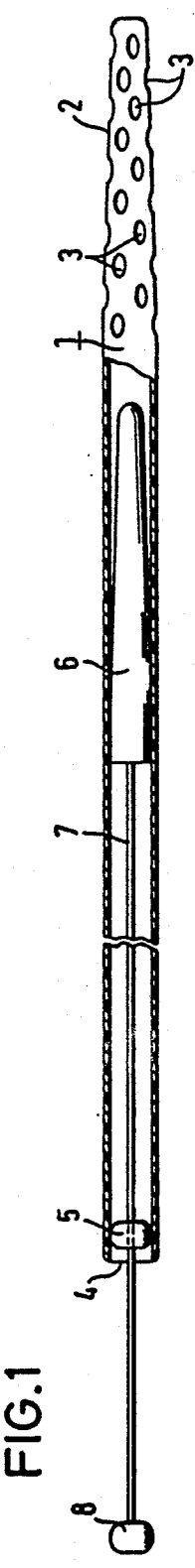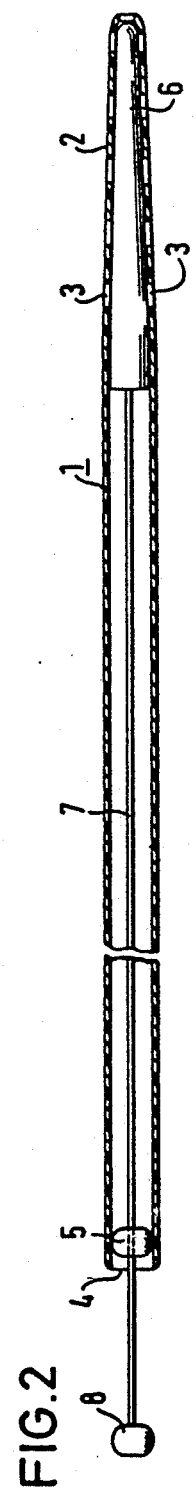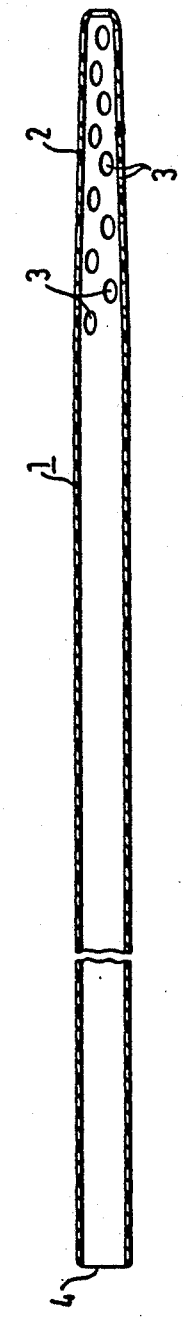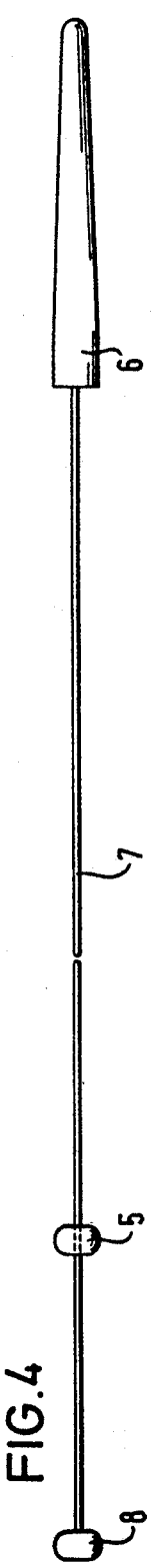

VASCULAR CATHETER

This is a continuation of application Ser. No. 880,762, filed on 7/1/86, now abandoned.

BACKGROUND OF THE INVENTION

The invention relates to a vascular catheter for cannulating arterial or venous vessels, for example, in the femoral region, or the vena cava and the right auricle of the heart, comprising of a flexible tube having blood passage orifices in the nature of holes at its anterior end (insertion end) to be inserted in the vessel or auricle as the case may be, the other end of the tube being directly or indirectly connectable to some other conduit or instrument.

Such catheters are employed in particular as venous return catheters in connection with heart-lung machines, which in cardiac surgery temporarily assume the function of the patient's heart and lungs. The purpose served by the catheter is to draw the blood returning to the patient's heart form the right auricle, or the inferior vena cava opening thereinto, and supply it to the heart-lung machine, or the pump to circulate the blood.

U.S. Pat. No. 4,129,129 discloses a return catheter of the kind mentioned above, which at its insertion tip comprises a first basket with elongated blood inlet orifices and, at a distance from this insertion tip, a second basket with additional elongated blood inlet orifices. In use, the first basket of this catheter is passed through the auricle of the heart into the inferior vena cava, bringing the second basket into the right auricle. This counteracts a reduction of venous drainage brought about by distortion of the arterial walls and of the vena cava or by change of position of the catheter.

A single catheter cannulation is also described in the reference "Single Catheter Gravity Drainage of the Right Atrium or Right Ventricle During Total Cardiac Bypass," by G. C. Blanco, et al., *Dis. Chest*, 35, pg. 554–560, May 1959. On page 555 of this reference, the catheter is shown to have multiple perforations in the distal portion of its body, and is positioned so that these perforations extend from the right atrium down to the inferior vena cava. The perforations are in such a position that they collect blood from both the right atrium and the inferior vena cava utilizing a single catheter.

With these and most other known catheters having blood passage orifices distributed along the length of the catheter, however, the problem raises that from the commencement of insertion of the catheter in the vessel or the auricle, blood enters through the foremost orifices at the insertion tip. Therefore, the insertion of the catheter must take place slowly and with care. As the orifices in the catheter are placed in the auricle or vessel the blood fills the tube, and a considerable quantity of blood may escape from the vessel, or the auricle, into the patient's body.

SUMMARY OF THE INVENTION

An object of the present invention is to dependably eliminate this disadvantage by the simplest possible means. This is accomplished, according to the invention, in that a piston-like closure member is movable to and fro in the catheter tube in the lengthwise direction thereof in such manner that it covers and thereby closes at least some of the blood passage orifices in other positions. Preferably, the closure member is so fashioned that it covers all blood passage orifices in one position in the tube, and clears these orifices in the insertion end of the catheter tube when in the closure position.

It becomes possible to therefore prevent any penetration of blood into the anterior insertion end, with the hazard of its reemergence through orifices located behind, during the insertion of the catheter, until the catheter with all its blood passage orifices has been inserted in the vessel or the auricle. This is effected by closure of the blood passage orifices, at least the foremost orifices, in the insertion end of the catheter tube, by the piston-like closure member displaceable therein. After total insertion of the catheter with its insertion end in the vessel, or the auricle as the case may be, the blood passage orifices may be opened by retracing the closure member, or extracting it from the catheter tube. Prior to the withdrawal of the closure member from the catheter tube, the latter may be clamped at a point outside the vessel or the auricle. To secure a tight closure of the blood passage orifices in the catheter tube, the closure member should be in contact with the edges of the orifices at the wall of the tube in its position of closing the orifices. To this end, it is expedient that the side wall of the closure member be substantially parallel to the side wall of the tube end comprising the blood passage orifices.

To the piston-like closure member there may advantageously be attached an actuating cable extending in the catheter tube more or less as far as its open tube end opposed to the insertion end, or protruding from the catheter tube at this open tube end. By means of this actuating cable, the closure member may be moved into and out of its closure position and withdrawn from the catheter tube as required.

Advantageously, a sealing plug is arranged in the catheter tube at a distance from the insertion end comprising the blood passage orifices, which plug may be displaceably seated on the actuating cable and withdrawn from the catheter tube together with the closure member. In this way, even if the closure member does not effect a complete coverage and closure of the blood passage orifices, emergence of blood from the catheter tube at its open posterior end before the tube can be connected to the tubing of the heart-lung machine or other appliance is avoided, and ruled out even upon movement of the closure member out of its closure position in the catheter tube. If the closure member is removed from the catheter tube by way of its open posterior tube end, connection of the catheter to the tubing system or the like is possible only after removal of the closure member. In so doing, the closure member can be moved as far as the aforesaid plug with the posterior tube end of the catheter sealed off by the plug, whereupon the catheter tube may be clamped ahead of the closure member, so that the closure member with plug may be pulled without allowing blood to escape from the catheter tube before it is connected to the tubing system or the like.

Nothing of this sort is possible in the case of the cardiac catheter of U.S. Pat. No. 4,129,129, although in that catheter a means is provided whereby blood having penetrated through the first basket into the tip of the catheter may be prevented from reemerging from the catheter tube through the second orifice basket behind during the insertion of the catheter. This known means consists in that the foremost end of the catheter tube comprising the first orifice basket is of smaller diameter than the portion of the catheter tube behind it comprising the second orifice basket, and that a sealing tube may be inserted in this foremost catheter tube of smaller diameter, which sealing tube keeps the blood having entered the tip of the catheter away from the orifices of the second basket. This sealing tube may be clamped at its posterior end protruding from the catheter and extracted from the catheter tube when the latter has been inserted together with its second orifice basket also into the auricle or the vena cava as the case may be.

In this known catheter, however, since the said sealing tube does not seal the blood passage orifices of the second basket, blood does enter the catheter through these orifices as soon as the second basket has been inserted into the auricle or the vena cava. Since the posterior open end of the catheter must not be closed prior to connection of the catheter to the tubing of the heart-lung machine or other appliance, so that the sealing tube may first be withdrawn from the catheter, this blood having entered the catheter will unavoidably emerge from the posterior open end of the catheter until this end of the catheter has been connected to the tubing or the like.

Other advantageous modifications of the catheter according to the invention are described elsewhere in the present application.

BRIEF DESCRIPTION OF THE DRAWINGS

The drawings represent, by way of example, especially advantageous embodiments of the catheter according to the invention, which embodiments will now be described in more detail.

FIG. 1 shows a side view of an embodiment of the invention in partial section, with the blood passage orifices open.

FIG. 2 shows a longitudinal section of this embodiment, with the blood passage orifices closed.

FIG. 3 shows a longitudinal section of this embodiment with the closure member removed.

FIG. 4 shows the closure member without the catheter tube.

DETAILED DESCRIPTION OF THE PREFERRED EMBODIMENTS

Figure 5:
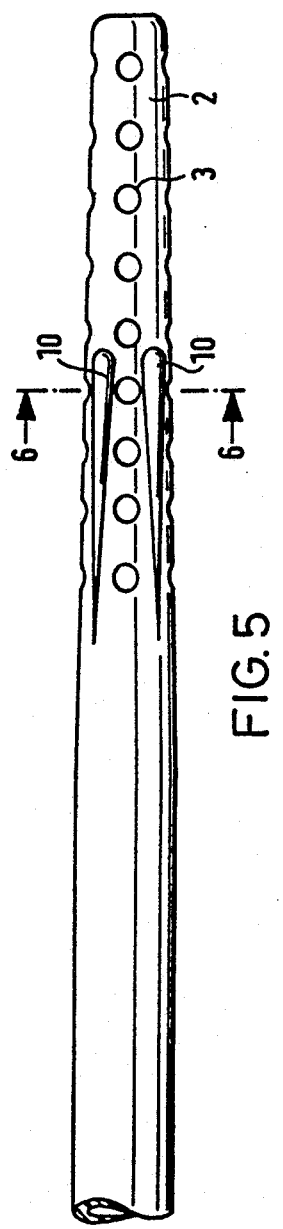
FIG. 5 shows a side view of an alternate embodiment in partial section of the invention.

In the embodiment represented by way of example in FIGS. 1 to 4, the catheter tube 1 is provided at its slightly tapered insertion end 2 with blood passage orifices 3 uniformly distributed over its periphery and over a portion of the length of the catheter. The catheter tube is closed off at its open posterior end 4 by a plug 5, displaceable in close contact with the inside wall of the catheter tube. In the interior of the catheter tube, a piston-like closure member 6 is arranged, movable to and fro in the catheter tube 1 in the lengthwise direction thereof. For this purpose, the closure member 6 is connected at its posterior end to an actuating cable 7 extending displaceably through the plug 5 and out of the posterior open end 4 of the catheter tube 1, and provided at its exterior end with a handle 8.

In FIG. 2, the closure member 6 is shown in its foremost position, covering the blood passage orifices 3. The closure member is matched in shape and dimensions to those of the interior of the insertion end 2 of the catheter tube 1 so that it will be in close contact with the edges of all blood passage orifices 3 in this position, in order to be able to close these orifices. The piston-like closure member has a likewise conical shape, this closure member being tapered more or less parallel to the conicity of the insertion end 3 of the catheter tube at its anterior end away from the actuating cable 7. The axial length of the closure member is so proportioned that in its closure position as shown in FIG. 2, it extends over the whole of the insertion end 2 of the catheter tube comprising the passage orifices 3. The blood passage orifices 3 in turn extend over an axial length of the catheter tube 1 in the region of its insertion end 2, slightly less than the catheter length to be inserted in the vessel or the auricle as the case may be.

With the closure member 6 brought into closure position as in FIG. 2, the catheter is carefully inserted into the vessel or auricle through an incision made in the vessel or heart wall far enough so that all blood passage orifices are inside the vessel or auricle. No blood can enter the catheter tube 1 through the sealed passage orifices. Should a small quantity of blood penetrate after all, it is prevented from escaping by the sealing plug 5 in the catheter tube.

After complete insertion of the catheter tube with its insertion end 2 in the leading position, the closure member 6 may be retracted by means of the actuating cable 7 as far as the sealing plug 5 or nearby thereto, whereby the blood passage orifices 3 are cleared and blood enters the catheter tube through them. However, owing to the sealing plug 5 and the closure member at least partially in contact or in substantial contact with the wall of the catheter tube 1, this blood cannot escape through the open end 4 of the catheter tube. Now the catheter tube may be clamped between its insertion end inserted in the vessel or auricle and the retracted closure member 6, whereupon closure member 6 with sealing plug 5 may be extracted from the catheter tube 1 and the latter connected at its posterior open end to a system of tubing or an appliance, for example a liquid pump.

Figure 6:
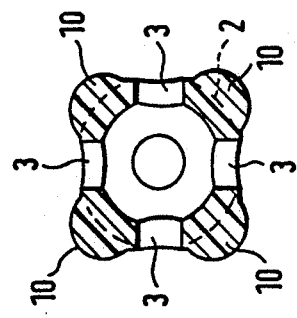
FIG. 6 shows an cross sectional view of this alternate embodiment taken along lines 6—6 of FIG. 5.

FIGS. 5 and 6 illustrate an alternate embodiment of the invention having a catheter tube in which a plurality of integral longitudinal ribs 10 are evenly distributed circumferentially around a portion of the anterior insertion end 2. The longitudinal ribs 10 are provided for reinforcement and stabilization of the catheter and to aid in keeping surrounding tissue from occluding the blood passage orifices 3.

Further modifications will occur to those skilled in the art. The scope of the invention is defined by the appended claims and should not be understood as limited by the specific embodiments described herein.

We claim:

1. A method for connecting a venous return of a heart-lung machine to the heart of a patient during open heart surgery which includes a vascular catheter comprising a flexible plastic tube having blood passage orifices along the wall of the anterior portion which is to be inserted into the heart auricle or vessel, and having means for connecting the posterior open end of the tube to the heart-lung machine, a piston-like closure member displaceable within the tube and capable of closing the orifices in an advanced position and clearing the orifices in a retracted position, an actuating means attached to the closure member and extending outwardly from the posterior end of the tube, a sealing plug in close contact with the inner wall of the posterior portion of the catheter and removable with the retracting of the closure member, with the method comprising the steps of:

advancing the closure member, so that it closes the blood passage orifices of the catheter;

inserting the anterior portion of the catheter into the desired location of the heart or vessel whereby no blood enters the catheter;

operating the actuating means thereby displacing the piston-like closure member into a retracted position whereby the orifices of the catheter are cleared permitting blood to flow into the catheter;

clamping-off the catheter at a location forward of the closure member;

retracting the actuating means, sealing plug and closure member from the catheter;

attaching the posterior end of the catheter to the heart-lung machine; and opening the clamping-off of the catheter whereby the venous return of the patient is connected to the heart-lung machine with no loss of blood and no introduction of air.

2. The method as in claim 1 wherein the catheter actuating means includes a cable.

3. The method as in claim 1 wherein the piston-like closure member is in close contact within the tube of the catheter whereby the retracting of the member creates a relative positive pressure within the posterior portion to force any air from the catheter and which creates a relative negative pressure in the anterior portion to smoothly draw blood into the catheter.

* * * * *